(12) United States Patent
Ruohonen et al.

(10) Patent No.: US 6,849,040 B2
(45) Date of Patent: Feb. 1, 2005

(54) METHOD AND APPARATUS FOR DOSE COMPUTATION OF MAGNETIC STIMULATION

(75) Inventors: Jarmo Ruohonen, Vantaa (FI); Jari Karhu, Kuopio (FI)

(73) Assignee: Nexstim Oy, Helsinki (FI)

( * ) Notice: Subject to any disclaimer, the term of this patent is extended or adjusted under 35 U.S.C. 154(b) by 0 days.

(21) Appl. No.: 10/272,355

(22) Filed: Oct. 15, 2002

(65) Prior Publication Data

US 2003/0073899 A1 Apr. 17, 2003

(30) Foreign Application Priority Data

Oct. 17, 2001 (FI) .............................................. 20012017

(51) Int. Cl.$^7$ ................................................ A61N 1/00
(52) U.S. Cl. ............................................ 600/14; 607/2
(58) Field of Search ............................................. 607/2

(56) References Cited

U.S. PATENT DOCUMENTS

| | | | |
|---|---|---|---|
| 4,167,190 A | * 9/1979 | Sorenson et al. | 607/59 |
| 5,116,304 A | * 5/1992 | Cadwell | 600/13 |
| 6,179,771 B1 | 1/2001 | Mueller | |
| 6,198,958 B1 | 3/2001 | Ives et al. | |
| 2001/0021794 A1 | * 9/2001 | Muraki et al. | 600/9 |
| 2003/0004392 A1 | * 1/2003 | Tanner et al. | 600/9 |
| 2003/0065243 A1 | * 4/2003 | Tanner | 600/9 |

FOREIGN PATENT DOCUMENTS

JP         08-280820        10/1996

* cited by examiner

*Primary Examiner*—Samuel G. Gilbert
(74) *Attorney, Agent, or Firm*—Smith-Hill and Bedell

(57) ABSTRACT

The invention relates to a method for determining the effect of magnetic stimulation on human brain. According to the method, the stimulation dose is determined in different parts of the brain by summing cumulatively the electric field strength generated by the individual stimulus pulses. According to the invention, the position and alignment of a magnetic stimulation coil (1) is determined separately for each applied stimulus pulse in three dimensions relative to the head (5), the number, repetition rate and intensity generated by the magnetic stimulation coil (1) are measured separately for each pulse, the coordinate data of the brain are determined substantially unambiguously in the same coordinate system with the magnetic stimulation coil (1) on the basis of information obtained from other kind of measurement, such as a tomographic scan or, e.g., a statistic database collected from a large number of patients, and the cumulative dose of electromagnetic radiation imposed on said desired point in the brain is determined on the basis of the location data available from the brain and the measurement data computed for the cumulative effect of the electromagnetic field evoked by said magnetic stimulation coil (1).

21 Claims, 1 Drawing Sheet

METHOD AND APPARATUS FOR DOSE COMPUTATION OF MAGNETIC STIMULATION

Figure 1:
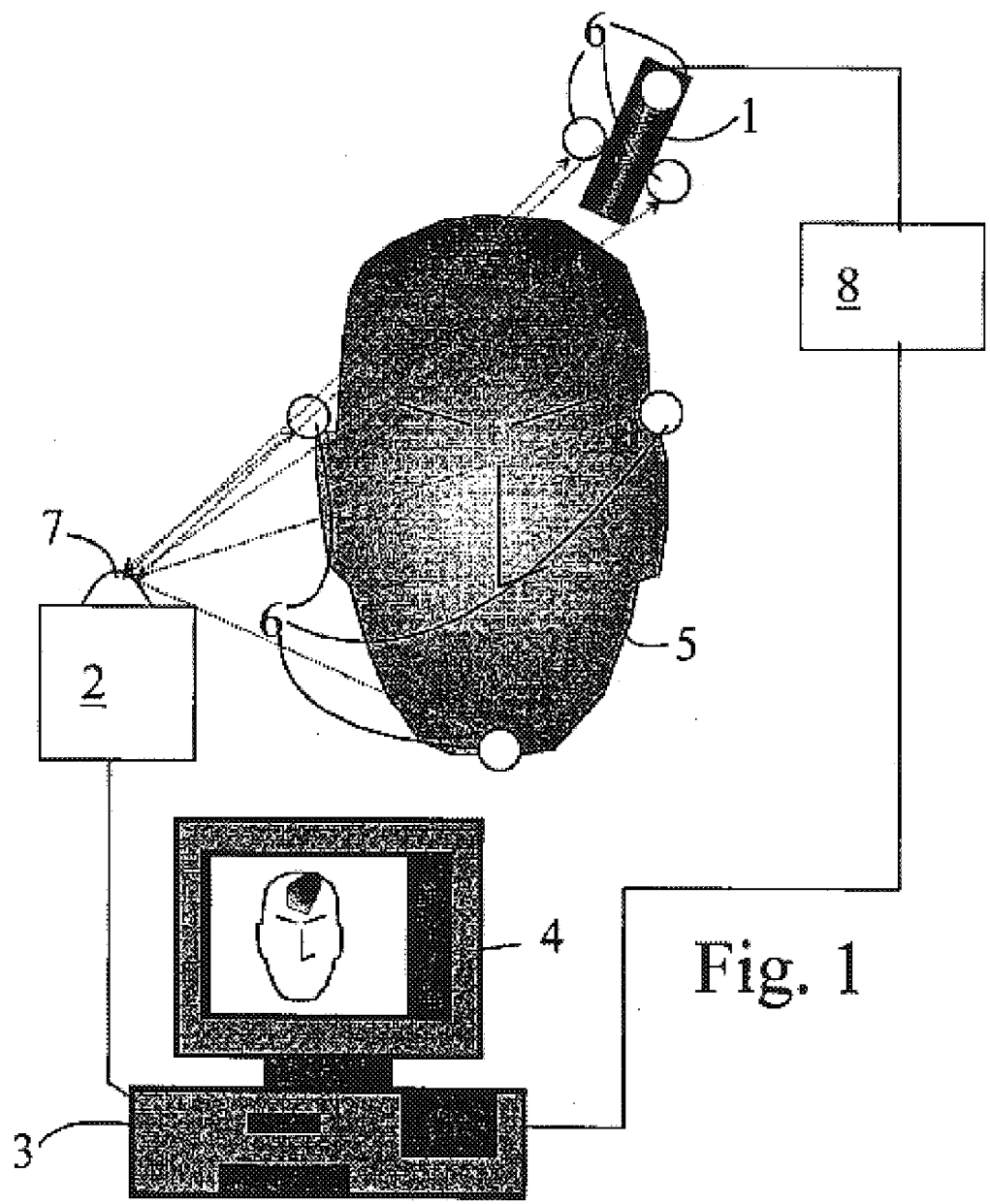

The invention relates to a method and apparatus for dose computation of magnetic stimulation.

Methods and apparatuses of the kind discussed herein are used for measurements, research and therapy applied on biological tissue through stimulating the tissue by electromagnetic means.

Using conventional techniques, it is possible to stimulate biological tissue such as the brain, the peripheral nervous system, muscles and the heart by virtue of inducing an electric field in the tissue. In magnetic stimulation, the induction of the electric field is accomplished by means of a changing magnetic field. An known, an electric field generates in a conducting tissue an electric current that stimulates the tissue. Different types of apparatus constructions based on magnetic stimulation are described, e.g., in U.S. Pat. Nos. 4,940,453; 5,047,005; 5,061,234; 5,066,272 and 5,267,938.

Magnetic stimulation offers a risk- and pain-free method of stimulating human brain, peripheral nervous system or muscles. The activation of nervous system cells by the electric current induced by magnetic stimulation may be utilized in plural manners. For instance, the stimulation of certain cortical areas triggers the contraction of the muscles controlling the functions of the hand thus permitting the velocities of nerve conduction from the brain to the muscles to be measured. The stimulation of certain other areas can be employed to interfere with the normal function of the brain, e.g., during the execution of a given task thus allowing the cortical areas related to the control of different tasks to be localized. Furthermore, the stimulation of certain regions of the brain by fast-rate trains of pulses may also have therapeutic effects; for instance, patients suffering from depressions have been reported to gain relief from the stimulation of the prefrontal cortical areas. Furthermore, trains of magnetic pulses may be used for modulating the response of the cortex: research reports have been published indicating that, e.g., application of a focused train of stimulation pulses may shorten the response delay measured after the stimulation pulse train.

The stimulating magnetic field is established by means of a coil wound from a conducting wire material through which a strong current pulse of short duration is passed. Resultingly, the coil generates about itself a magnetic field whose strength decays rapidly at a greater distance from the coil. Respectively also is attenuated the stimulating effect of the time-varying magnetic field on living tissue. The field pattern about the coil and thereunder is dependent on the shape of the coil. Magnetic stimulation is characterized in that even so small a deviation of 5 to 10 mm in the location of the coil or a tilt of 10° in the orientation thereof may change the stimulating effect at the target location as much as 50%. The stimulus amplitude can be controlled by varying either the amplitude or waveform of the current pulse applied to the coil.

In a plurality of applications, predetermined regions of the brain are stimulated by fast-rate trains of stimulation pulses. Reports on this kind of application can be found in scientific publications. In depression therapy, for instance, the stimuli are generally given at a rate of 20 pulses/s for about one minute. The stimulus pulse trains are given several times in a sequence and during several days. In almost all of these applications it is vital that the stimulating electric current is generated in a correct region of the brain which in depression therapy specifically is the left frontal lobe of the brain. The therapeutic or other effect gained from the stimulation is dependent on the overall number of pulses. The effect is further dependent on the rate of the applied pulse train and the overall duration of the pulse train.

If the stimulation is applied as fast-rate pulse trains and/or at high intensity on a single region of the brain, adverse effects may arise in the form of an epileptic seizure, for instance.

Conventionally, the stimulus intensity is determined by comparing the effect of the stimulus with such a stimulus threshold intensity that is required for the activation of the motor cortex at the area controlling the movement of the hand. The response of this area is detectable as a twitch of the muscles controlled by the cortical area. Such a stimulus intensity is called the threshold stimulus of the motor cortex. It must be noted that when a stimulus intensity lower than that of the threshold stimulus is used, no immediately detectable response to the stimulus will be obtained. Similarly, when a number of different cortical areas are stimulated, such as the frontal lobe as a whole, it is possible that stimulus intensities even higher than the motor excitation threshold stimulus may be applied without causing any immediate detectable response to the stimulus. However, if the stimulation is applied in pulse trains, a temporary or longer-lasting modulating effect on the function of the stimulated cortical area may be found.

One problem hampering the use of conventional methods and equipment is that they do not permit accurate estimation of stimulus intensity or dose in different parts of the brain. It is not possible to make even a coarse assessment generally in other areas except when the motor cortex is being stimulated inasmuch as herein the stimulus evokes an easily detectable physiological response as soon as the stimulus exceeds a given threshold value.

Another problem is caused by the fact that the sulci of the cortex may be located at different distances from the scalp when different individuals are compared with each other in regard to the different regions of their brain. As a result, conventional methods and equipment are ill suited for assessing the magnitude of the stimulating electric current at the desired target region.

A third problem hampering the use of prior-art techniques and systems is that the threshold intensity of magnetic stimulation applied on the motor cortex is significantly affected by plural uncontrollable factors such as drugs and the level of alertness. Furthermore, tensioning of the muscles controlled by the target region prior to the stimulation thereof may lower the stimulus threshold appreciably. Hence, mere comparison of the stimulus with the motor activation threshold stimulus may give a distorted view on the effective intensity of the stimulus on some other area of the cortex. For the same reason, a correspondence between the intensity of an applied electromagnetic field and its physiological effect cannot be established when the field is applied on the brains of different test individuals or patients.

A fourth problem hampering conventional methods and equipment is that if the coil is moved during a test or therapeutic session, the maximum effect of the stimulus is shifted onto a different part of the cortex, whereby also the response changes from that originally intended.

It is an object of the invention to eliminate the shortcomings of the above-described prior art and to provide an entirely novel type of method suited for estimation of the summed effect of stimulation on any cortical area individually for any test person to be stimulated. The goal of the invention is achieved by way of accurately computing the applied dose of stimulation and then accumulating this information during an ongoing stimulation session.

The invention is based on a method comprising the steps of determining the electromagnetic field generated by the coil, the position and alignment of the coil relative to the head and computing the electric field after each stimulus pulse for cortical areas determined from anatomic pictures of the test person's head. Thereupon, the stimulus dose is computed as a cumulative electric field strength summed from the electric field values imposed on different parts of the brain during a train of stimulus pulses. Additionally, an effective dose may be computed such that takes into account the duration of time over which the dose being applied was administered and the number of pulses per second administered.

While the invention advantageously uses electromagnetic or optical sensor techniques for determining the position and alignment of the coil in regard to the head, also other position location methods may be used. Advantageously, the anatomy of the test person's head is determined by magnetic imaging. The electric field induced by the coil may be advantageously determined very accurately by first computing the magnetic field generated by the coil, whereupon a tissue conductivity model is created representing the head of the test person being stimulated and then the model is utilized in computations based on conventional mathematical methods for determining the electric field generated by the time-varying magnetic field through electromagnetic induction in the tissue. Accurate computational models of this kind are known from the literature of the art.

The invention facilitates accurate and even precomputed assessment of stimulus dose to be administered on different parts of the brain. This feature is particularly vital when the stimulus is to be administered therapeutically, that is, in the same fashion as any drug. Furthermore, the computed cumulative and effective dose values may be utilized to assess the therapeutic or other effect to be expected from the stimulation.

The invention offers significant benefits.

One of the benefits features accurate application of a desired cumulative or effective dose on a given cortical area as is necessary in a therapeutic session, for instance.

A second benefit is the facility of monitoring during an examination session the safety margin of the examination and to determine the cumulative stimulus dose imposed on the cortex that should not exceed a given limit at which magnetic stimulation must be stopped in the interest of safety.

A third benefit is that the assessment of the cumulative dose and effective dose received by different test persons can be used for developing and monitoring the patient safety of magnetic stimulation and, further, for accurate comparison of the effects of magnetic stimulation between different persons.

In this fashion, the planning and realtime monitoring of the administration of a cumulative stimulus dose or an effective stimulus dose may help minimizing the possible adverse effects of magnetic stimulation.

In the following, the invention will be examined in greater detail with the help of exemplifying embodiments by making reference to the appended drawing illustrating a preferred embodiment of the invention, wherein FIG. 1 shows the layout of an apparatus suited for dose computation.

In the apparatus of FIG. 1, the position and alignment of coil 1 relative to head 5 is determined with the help of a location device 2. After the position and alignment of coil 1 as well as of the head are thus known unambiguously, also the effective range of the electromagnetic field generated by coil 1 inside the head can be determined after the instantaneous value of the stimulation current applied to the coil is known. Obviously, the use of the method requires additional information obtainable from a three-dimensional model of the electromagnetic field generated by the coil as a function of drive current of the coil. The measured position coordinates of head 5 and coil 1 are submitted to a computer 3 that computes the electromagnetic field generated in the head 5. The field strength and the dose applied during the stimulation session are displayed to the system operator on screen 4. The dose is computed as a sum of the applied electric field/electric current at any desired point. In the computation of the effective dose, the factors to be taken into account include the repetition rate in trains of stimulus pulses and the possible differences between the separate pulses in the magnitude of the induced electric field.

The magnetic stimulator 8 driving coil 1 submits information to computer 3 on the relative intensity of the applied stimulation. Herein it is sufficient to know the electric field as determined at one stimulation intensity. Additionally, computer 3 is used for monitoring the number and application rate of the stimulus pulses. The computer may also control the intensity of stimulation and start instant of stimulus pulse trains administered by stimulator 8 thus making it possible to automate the administration of the stimulus dose and computation of its effect in the brain.

An embodiment of the invention is adapted to determine the electric field strength in the brain and to visualize the same by colors or tones in pictures taken using magnetic resonance imaging. After the electric field strength is determined separately for each stimulus pulse, the cumulative effect of the stimulus pulses may be assessed by either summing the effects of the pulses or using a priori information obtained by experiments. By virtue of these techniques, the stimulation dose can be monitored in real time over the entire duration of the stimulation session.

Without departing from the scope of the invention, embodiments different from those described above may be contemplated.

In an alternative arrangement, the operator of the stimulation apparatus 8 first defines on the screen 4 in the MRI pictures taken from the patient's head such cortical areas that are to be stimulated. Thereupon, the operator presets a desired cumulative dose or effective dose and the distribution thereof in the brain. With the help of the realtime location of the coil and interactive computer software, the operator controls the coil 1 into an optimal position, whereupon stimulation is commenced. Computer software monitors changes in the position and alignment of coil 1, as well as changes in the amplitudes of stimulus pulses, and computes the dose distribution in real time individually for each stimulus pulse. The software may include visualization and interactively request the operator to move coil 1 or change the intensity of the stimulus pulses so that the desired dose will be accomplished. After the desired dose has been administered, computer 3 requests the operator to shut off stimulation or performs this steps automatically.

In a still another embodiment, coil 1 of magnetic stimulator 8 is connected to a robot (not shown in the diagram) controlled by computer 3. This arrangement makes it possible to automate the administration of a desired dose.

In a further another embodiment of the invention, head 5 of the person being tested or treated bears a position sensor whose position and alignment can be sensed by a location system 2. The sensor may be mounted on the shafts of eyeglasses, for instance. Next, the same location system is employed for locating the anatomical landmarks of the head relative to the position sensor. The landmarks are identified on the MRI pictures. On coil 1 is mounted a second position sensor adapted to sense the coil position and alignment. With the help of this arrangement having the position and alignment of sensors mounted on both head 5 and coil 1 measured simultaneously, it is possible to determine the position and alignment of coil 1 relative to head 5 and the preselected position coordinate points of the head, whereupon conventional coordinate conversion techniques may be used to identify any respective point on the MRI pictures of the head. The location system may be based on the use of visible light, infrared light or electromagnetic fields. The number of head fiducials must be at least three on different sides of the head. Conventionally, the fiducials are selected to be the so-called preauricular points nasally in front of the left and right ear and the nose nick, or the nasion. In the diagram, the position sensors are denoted by their fiducials 6. Each sensor must include at least three fiducials 6 for unambiguous identification thereof in a three-dimensional space. The fiducials may be entirely passive, such as simple reflectors that return the signal emitted by the antenna 7 of the location system 2 or, alternatively, the fiducials 6 may be equipped with active transmitters operating at a suitable wavelength band of electromagnetic radiation. The location of fiducials may be based, e.g., on transmission phase or delay detection between the fiducials and location system antenna 7.

As an alternative arrangement to those described above, the invention may be implemented so that the position of coil 1 is determined from the position coordinates of a mechanical system such as a robot connected to the coil. In a similar fashion, also the position coordinates of the head may be obtained by supporting head 5 at predetermined points by support arms or the like, whereby mechanical means such as robotic actuators may be used for unambiguous determination of the position and alignment of both the head 5 and the coil 1 relative to each other.

The computation of the dose effect invoked by an electric field in a three-dimensional space is described below:

The dose of magnetic stimulation imposed on a given point (X,Y,Z) of the brain is a function of the electric field E of stimulus pulses imposed on the point. The dose contribution of a single pulse is computed as follows:

$$\text{Dose (at point } X,Y,Z) = \int f(E(X,Y,Z,t))dt,$$

where integration is performed over the duration of the magnetic stimulus pulse.

Advantageously, function f above is defined as:

f=|E|, when |E|>$E_T$, where $E_T$ is a threshold value;
f=0 otherwise.

Advantageously, the combined effective dose of multiple pulses is computed as the sum of the stimulus effects of the individual pulses.

The threshold value $E_T$ may advantageously be defined to be, e.g., half of such an electric field strength that, imposed on the motor cortex, on the average evokes a detectable motor response in physiologically normal test persons. Generally, this threshold field strength is in the order of 100 V/m. Depending on the needs of different applications, the dose computation function f may be selected otherwise (e.g., f=|E|$^2$ when |E|>$E_T$, where $E_T$ is the threshold value; f=0 otherwise), and in certain applications it is also possible to include the repetition rate of the transcranial magnetic stimulation (TMS) pulses as a parameter of the dose function. Depending on the application, also the threshold value may be defined differently.

Having a vector character, the electric field E can be computed at a given instant of time t in a conventional fashion:

$$E(X,Y,Z,t) = -\partial A(X,Y,Z,t)/\partial t - \nabla V(X,Y,Z,t).$$

In the above equation, the vector potential A generated by the coil is computed using the methods described in the literature of electromagnetic fields. For the computation, information is needed on the coil geometry, position and location relative to point X,Y,Z, as well as the parameters of the current pulse passed through the coil. Also the electric potential V is computed by solving the Laplace equation $\nabla^2 V=0$ using methods known from the literature of art. The geometry of the head tissue conductivity must also be known for the computation. The most accurate results will be achieved by using finite-element methods in combination with conductivity data inferred from MRI pictures for the different areas of the test person's head.

While the effective dose of a therapeutic or research session can be basically computed by summing the doses imparted by the individual pulses of a stimulus pulse train (as described above), it is also necessary to refine the effective dose computation by taking into account the intervals separating the individual pulses of the pulse train in the following way:

$$\text{Effective dose (at point } X,Y,Z) = \Sigma(F \times \int f(E(X,Y,Z,t))dt),$$

where F is a coefficient having a value dependent on the repetition rate of the stimulus pulses and the dose is summed over the duration of the pulses in the stimulus pulse train. Function f is the same as above. The value of F increases with a higher pulse repetition rate. Investigations into the literature of magnetic stimulation permit a plausible assumption that F=1 for pulse repetition rates lower than 1 Hz, F=2 for 10 Hz pulse repetition rate, F=4 for 20 Hz pulse repetition rate, and F=6 for 30 Hz pulse repetition rate.

What is claimed is:

1. A method for determining the effect of magnetic stimulation on the brain of a human subject, the method comprising the steps:

applying a sequence of stimulus current pulses to a magnetic stimulation coil to induce an electric field in the brain, for each applied stimulus pulse, separately determining the position and alignment of the magnetic stimulation coil in three dimensions relative to the subject's head, determining coordinate data for the brain substantially unambiguously in the same coordinate system with the magnetic stimulation coil, calculating the intensity of the electric field induced at a desired point in the brain, or the electric current generated at said desired point, for each stimulus pulse applied to the magnetic stimulation coil, and calculating the cumulative dose of electric field induced at said desired point in the brain by summing the electric field intensity induced by the individual stimulus pulses over the sequence of pulses, or calculating the cumulative dose of electric current generated at said desired point in the brain by summing the electric currents generated by the individual stimulus pulses over the sequence of pulses.

2. A method according to claim 1, comprising graphically displaying the cumulative dose.

3. A method according to claim 1, comprising using the calculated value of the cumulative dose in assessing therapeutic effect of a magnetic stimulation treatment.

4. A method according to claim 3, comprising using the cumulative dose in monitoring safety of a patient undergoing magnetic stimulation treatment.

5. A method according to claim 1, comprising computing a value of effective dose by weighting the electric field intensity induced by the individual stimulus pulses, or the electric current generated at said desired point in the brain, using weighting coefficients representing known physiological effects.

6. The method according to claim 5, comprising using the effective dose in monitoring safety of a patient undergoing magnetic stimulation treatment.

7. A method according to claim 5, wherein the effective dose is used in comparison of physiological effects evoked by magnetic stimulation in different test subjects or subject groups.

8. A method according to claim 1, wherein the cumulative dose is used in comparison of physiological effects evoked by magnetic stimulation in different test subjects or subject groups.

9. A method according to claim 1, comprising recording the brain anatomy by magnetic resonance imaging.

10. A method according to claim 1, comprising displaying the dose on an anatomic picture.

11. A method according to claim 1, comprising determining the dose in real time and using the dose as thus determined for real time monitoring.

12. A method according to claim 1, comprising monitoring the dose in real time fashion and terminating stimulation if a preset stimulus dose limit value is exceeded on any or a preset region of the brain.

13. A method according to claim 1, comprising displaying the results of the dose computation in colors and tones on brain pictures acquired by magnetic imaging.

14. An apparatus for stimulation of living tissue such as the brain of a human subject, the apparatus comprising:

a magnetic stimulation coil, a location device for measuring the position and alignment of the coil relative to the subject's head, a magnetic stimulator connected to the coil for supplying a sequence of current stimulus pulses to the coil, and a computer for calculating relative intensity of the electric field induced by consecutive current pulses, computing from the position and alignment of the coil the magnitude of electric field induced in different parts of the brain, or the electric current generated in different parts of the brain by the electric field, and computing a stimulation dose after applying the sequence of stimulus pulses by Bumming the magnitudes of the electric field or current at desired points in the brain over the sequence of pulses.

15. Apparatus according to claim 14, wherein the location device is a device that emits infrared light.

16. Apparatus according to claim 14, wherein the location device measures the location and alignment of both the coil and the subject's head.

17. Apparatus according to claim 14, including a means for emitting a warning when a maximum limit value of the applied dose is exceeded.

18. Apparatus according to claim 14, including a means for weighting the doses of the stimulus pulse trains by repetition rate in order to compute the effective dose.

19. Apparatus according to claim 18, including robotic means for controlling the coil such that the effective dose will be automatically administered on a predetermined brain region.

20. Apparatus according to claim 14, including robotic means for controlling the coil such that the cumulative dose will be automatically administered on a predetermined brain region.

21. Apparatus according to claim 14, including a mechanical means for determining the position of both the coil and the subject's head.

* * * * *